United States Patent
Bassan, Jr.

(10) Patent No.: US 9,307,755 B1
(45) Date of Patent: Apr. 12, 2016

(54) TEPHRITID CONTROL SYSTEM

(76) Inventor: Morton Edward Bassan, Jr., Naalehu, HI (US)

(*) Notice: Subject to any disclaimer, the term of this patent is extended or adjusted under 35 U.S.C. 154(b) by 685 days.

(21) Appl. No.: 13/369,058

(22) Filed: Feb. 8, 2012

Related U.S. Application Data (60) Provisional application No. 61/440,795, filed on Feb. 8, 2011.

(51) Int. Cl.
| | | |
|---|---|---|
| *A01M 1/00* | (2006.01) | |
| *A01N 27/00* | (2006.01) | |
| *A01N 25/02* | (2006.01) | |
| *A01N 31/00* | (2006.01) | |
| *A01N 35/00* | (2006.01) | |
| *A01N 43/00* | (2006.01) | |
| *A01N 43/24* | (2006.01) | |
| *A01N 25/00* | (2006.01) | |
| *A01M 1/02* | (2006.01) | |
| *A01M 1/10* | (2006.01) | |
| *A01M 1/20* | (2006.01) | |

(52) U.S. Cl.
CPC . *A01M 1/00* (2013.01); *A01N 27/00* (2013.01)

(58) Field of Classification Search
CPC ....... A01N 25/00; A01N 25/02; A01N 27/00; A01N 31/00; A01N 35/00; A01N 43/00; A01N 43/24; A01M 1/00; A01M 1/02; A01M 1/106; A01M 1/2016; A01M 2200/012
USPC .................................................. 424/84, 410
See application file for complete search history.

(56) References Cited

U.S. PATENT DOCUMENTS

| | | | | |
|---|---|---|---|---|
| 7,887,828 | B2* | 2/2011 | Mafra-Neto | A01N 43/20 424/409 |
| 8,007,820 | B2* | 8/2011 | Parker | A01N 43/22 424/406 |
| 2004/0208953 | A1* | 10/2004 | Heath | A01N 25/006 426/1 |
| 2008/0118461 | A1* | 5/2008 | Boucher, Jr. | A01N 43/22 424/84 |

OTHER PUBLICATIONS

Martin Jacobson, Insecticides, Insect Repellents, and Attractants from Arid/Semiarid-Land Plants, Compilation of References, 1947-1982, U.S. Dept. of Agriculture, Beltsville, MD, pp. 138-146; p. 143 misnumbered as p. 743; [online] [retrieved on Sep. 30, 2014]; Retrieved from the Internet: <URL: https://www.princeton.edu.pdf.*
"Methyl Eugenol", Office of Environmental Health Hazard Assessment [online], Mar. 2013, [retrieved Jun. 1, 2015] Retrieved from the Internet :<URL: http://oehha.ca.gov/pesticides/programs/pdf/HQA_Methyl%20Eugenol_2013.pdf.*
"Basil", Wikipedia [online], [retrieved Jun. 1, 2015] Retrieved from the Internet: <URL: http://en.wikipedia.org/wiki/Basiil>.*
"1-Octen-3-ol", Wikipedia [online], [retrieved Sep. 30, 2014] Retrieved from the Internet: <URL: http://en.wikipedia.org/wiki/1-Octen-3-ol>.*

(Continued)

*Primary Examiner* — Jane C Oswecki
(74) *Attorney, Agent, or Firm* — Michael D. Eisenberg (57) ABSTRACT

A system for controlling tephritid fruit flies, comprising a first lure module for attracting tephritid fruit flies to eat a toxicant and a second cooling module for lowing environmental temperature to a temperature lethal to fruit flies but above the ice crystallization of fruit. The lure comprises: wax; oil; ethyl methyl eugenol or other suitable attractant; and Spinosad or other suitable toxicant.

13 Claims, 11 Drawing Sheets

LURE MODULE 15

| Substance | Amount (by weight) |
|---|---|
| Wax | 67.8 |
| Oil | 82.5 |
| EME | 12.0 |
| Spinosad | 3.00 |

COOLING MODULE 20

(56) References Cited

OTHER PUBLICATIONS

Martin Jacobson, Insecticides, Insect Repellents, and Attractants from Arid/Semiarid-Land Plants, Compilation of References, 1047-1982, U.S. Dept. of Agriculture, Beltsville, MD, pp. 138-146; p. 143 misnumbered as p. 743; [online] [retrieved on Sep. 30, 2014]; Retrieved from the Internet: <URL: https://www.princeton.edu.pdf.*

"Methyl Eugenol", Office of Environmental Health Hazard Assessment [online], Mar. 2013, [retrieved Jun. 1, 2015] Retrieved from the Internet: <URL: http://oehha.ca.gov/pesticides/programs/pdf/HQA_Methyl%20Eugenol_2013.pdf.*

"Basil", Wikipedia [online], [retrieved Jun. 1, 2015] Retrieved from the Internet: <URL: http://en.wikipedia.org/wiki/Basil>.*

\* cited by examiner

LURE MODULE 15

| Substance | Amount (by weight) |
|---|---|
| Wax | 67.8 |
| Oil | 82.8 |
| EME | 12.0 |
| Spinosad | 8.00 |

Fig. 1A

COOLING MODULE 20

TEPHRITID CONTROL SYSTEM

CROSS-REFERENCES TO RELATED APPLICATIONS

The present application claims priority from U.S. Provisional Application Ser. No. 61/440,795 filed on Feb. 8, 2011, which is hereby incorporated herein by reference in its entirety.

TECHNICAL FIELD

The present invention, in some embodiments thereof, relates to a pest control system, particularly tephritid fruit flies.

BACKGROUND OF THE INVENTION

Tephritid fruit flies pose a serious problem in growing, storing and transporting fresh fruit. The present invention is an improvement on current methods for controlling fruit flies in the presence of fruit.

BRIEF SUMMARY OF EMBODIMENTS OF THE INVENTION (1) The present invention relates to system for controlling tephritid fruit flies. In a variant, a lure for attracting tephritid fruit flies, comprises: wax; oil; ethyl methyl eugenol; and Spinosad.

(2) In another variant of the tephritid fruit fly lure, the wax comprises bee's wax and the oil comprises mineral oil.

(3) In a further variant of the tephritid fruit fly lure, wherein the lure comprises: a ratio of wax to oil by weight of about 0.8188 to 1.0; a ratio of Spinosad to oil by weight of 0.0966 to 1.0; and 1 milliliter of ethyl methyl eugenol per 5.65 grams of wax.

(4) In still another variant of the tephritid fruit fly lure, the lure comprises: a ratio of wax to oil by weight from about 0.7711:1.0 to about 0.8694:1.0; a ratio of Spinosad to oil by weight from about 0.0909:1.0 to about 0.1026:1.0 and a ratio of ethyl methyl eugenol to wax of about 1 milliliter of ethyl methyl eugenol per 5.32 grams of wax to about 1 milliliter of ethyl methyl eugenol per 6.00 grams of wax;

(5) In yet a further variant of the tephritid fruit fly lure, the lure comprises: about 36.4% of wax by weight; about 44.4% of oil by weight; about 10.3% of ethyl methyl eugenol by weight; and about 7.7% of Spinosad by weight.

(6) In another variant of the tephritid fruit fly lure, the lure comprises about 0.12% of 1-OCTEN-3-OL by weight.

(7) In a further variant, a system for eliminating tephritid fruit flies comprises: a tephritid fruit fly lure of any of the preceding and a cooling system configured to cool environmental air temperature to a range below a temperature lethal to tephritids and above the ice crystallization temperature of a fruit.

(8) In still another variant of the system for eliminating tephritid fruit flies, the cooling system is configured to cool environmental temperature below the freezing point of water but above the ice crystallization temperature of a fruit.

(9) In yet a further variant, a method of eliminating tephritid fruit flies from fruit, comprises: placing a lure in proximity to the fruit, the lure comprising: wax; oil; ethyl methyl eugenol; and Spinosad; placing the fruit in a closed refrigerated compartment, without the lure; cooling the air temperature in the compartment to inside a range below a temperature lethal to tephritids and above the ice crystallization temperature of a fruit.

(10) In another variant, the method of eliminating tephritid fruit flies from fruit comprises: measuring the soluble solids in the fruit; computing the relative freezing point of the fruit where ice crystallization will occur; slowly acclimatizing the fruit to at or below the temperature lethal to tephritid fruit flies by slowly changing the temperature; cooling the fruit down to a core temperature that is above the ice crystallization temperature, but below the freezing point of water, for about 31-36 hours or optionally, the time period required for a-yet-to-be-USDA-APHIS approved sub-freezing quarantine protocol and slowly acclimatizing the fruit by warming it up to a shipping temperature.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The present invention may be employed to control insects by selecting the proper lure mixed with a wax and a wax thinning agent and the proper toxicant. Insects may include tephritid fruit flies, yellow jackets and cockroaches for example.

Figure 1A:
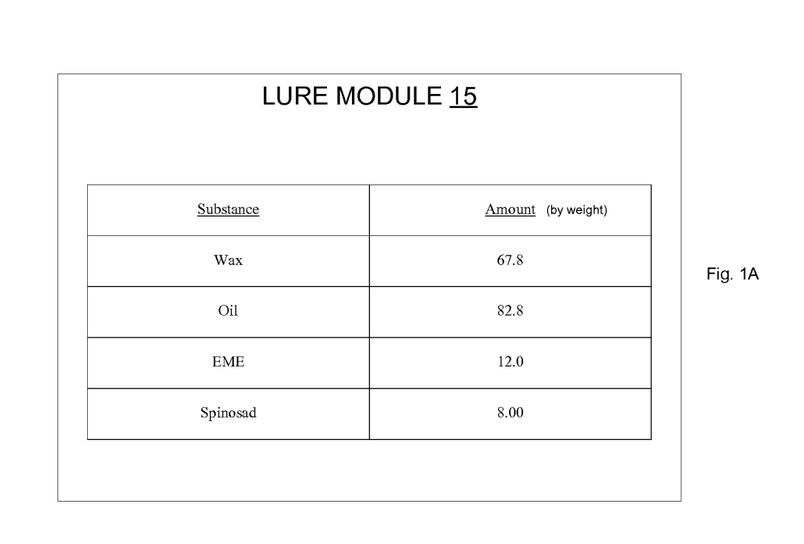
FIGS. 1A and 1B are block diagrams of a tephritid fruit fly control system.

The present invention is directed toward a Tephritid control system 10. In one variant, referring to FIG. 1, the control system comprises two modules. A first module is a lure system 15. The lure system may comprise natural bees' wax (optionally organic bees' wax) mixed with a human laxative mineral oil. The mineral oil makes the wax more pliable and easier for a Tephritid to eat by thinning the bees' wax. The lure system also includes a Tephritid pheromone and toxicant. Optionally, oil may be omitted from the lure. Optionally, other oil suitable for softening wax for tephritid mandibles to pierce and eat may be employed.

Any wax is suitable that is reasonably hard at room temperature and can be softened by incorporating mineral oil. Ambient air temperature coupled with how much the wax is thinned can be used to control the volatilization of the pheromone and toxicant and also allow the target insect's mandibles to pierce into the softened wax. When a target insect's mandibles pierce into the softened wax, that action opens a new little bubble of lure/toxicant to become even more attractive and toxic.

Of importance is to make sure that the waxy mixture becomes softened for the insect's mouth parts, while the melting temperature of the mixture is high enough to prevent melting from environmental factors like sun, heat and rain.

Using organic bee's wax allows the lure to be fully USDA certified organic.

Bees' wax (which melts at about 145° F.) combined with mineral oil forms a pliable mixture to makes the pheromone/toxicant less susceptible to rain and sun that normally causes rapid volatilization with rapid attraction and toxicity deterioration. In one variant, an electric whisk/beater is optionally used to beat as much air into the mixture as possible to make it easier for an insect's mandibles to pierce into the mixture, also causing new surface area to be created for controlled volatilization of the pheromones and flash toxicant.

In one example, to make 3,335.61 grams total lure mixture, 1213.80 grams bees' wax, 1482.34 grams mineral oil, 383.68 ml ethyl methyl eugenol (pheromone), and 255 grams 22.8% Spinosad (organic fermented excretion toxicant) are combined.

In one variant, components for a *Bactrocera* (previously known as genus "*Dacus*") *dorsalis* (Oriental fruit fly) lure comprise:
1. Bee's wax, by weight 36.4%
2. Mineral oil, by weight 44.4%
3. Ethyl methyl eugenol also known as methyl eugenol or lure, by weight 11.5%
4. Spinosad, by weight 7.7%
5. Unscented liquid dishwashing soap such as Palmolive® a few drops These proportions can be varied, to approximately these percentages.

In a variant, the lure may be formed as follows. In a double boiler barely melt the wax. In a separate jar mix the lure's attractant or pheromones with spinosad adding a few drops of dishwashing soap, watching the miscibility. As the wax melts add the mineral oil with an electric whisk type tool and mix very well beating in as much air as possible. As the mixture cools, notice a semi-hardening. As the wax/oil mixture is in the soft but hardening stage add the attractant/spinosad/soap whipping all ingredients together beating in as much air as possible. Keep beating until the mixture is too hard for your whisk to beat any more. Make sure that the whisk is moved all around to make the lure's total mixture as homogenous as possible. Let the mixture sit still until it settles which takes 12 to 24 hours.

In another variant, the oil may be derived from steam distilled sweet basil (*Ocimum basilicum* L.) into oil containing the following chemicals: _-pinene (1; C10H16), linalool (2; C10H18O), trans-anethole (3, C10H12O), 4-methoxy benzaldehyde (4; C8H8O2), estragole (5; C10H12O), 1-methoxy-4-(1-methoxypropyl)-benzene (6; C11H16O), trans-caryophyllene (7; C15H24), methyl eugenol (8; C11H14O2), 3,7,11-trimethyl-(E)-1,6-dodecatriene-3-ol (9; C15H26O), 2,3-dihydro-1H-Indene-5-ol (10; C9H19O), 3-[3-iodo-2-(iodomethyl)-2-methylpropyl]-1,2,4,5-tetramethyl benzene (11; C15H22I2), and 1-(1,1-dimethyl)-2-methoxy-4-methyl-3,5-dinitrobenzene (12; C12H16N2O5). Linalool (2), transanethole (3), and estragole (5) which are major volatile components in basil oil as published by CHIOU LING CHANG, IL KYU CHO, AND QING X. LI in the J. Econ. Entomol. 102(1): 203Ð209 (2009).

Other lures or lure combinations for other Tephritid may be prepared utilizing the principles of the invention. For example, methyl eugenol also attracts *Dacus zonatus* which is another serious Tephritid to be controlled by the present lure system.

The following table 1 illustrates four example lure mixtures generated.

TABLE 1

| Date | ml QTY | Bee's Wax | Mineral Oil | EME | 22.80% Spinosad |
|---|---|---|---|---|---|
| Friday Aug. 6, 2010 | 1 | 170.60 | 67.80 | 82.80 | 12.00 | 8.00 |
| Saturday Aug. 7, 2010 | 2 | 483.12 | 192.00 | 234.48 | 33.98 | 22.65 |
| Wednesday Aug. 11, 2010 | 3 | 1276.29 | 454.00 | 554.44 | 160.71 | 107.14 |
| Saturday Aug. 14, 2010 | 4 | 1405.60 | 500.00 | 610.62 | 176.99 | 117.99 |
|  | 5 |  |  |  |  |  |
| Totals | 23 | 3335.61 | 1213.80 | 1482.34 | 383.68 | 255.79 |
| Costs |  | $29.87 | $8.02 | $6.64 | $15.20 |  |

Figure 1B:
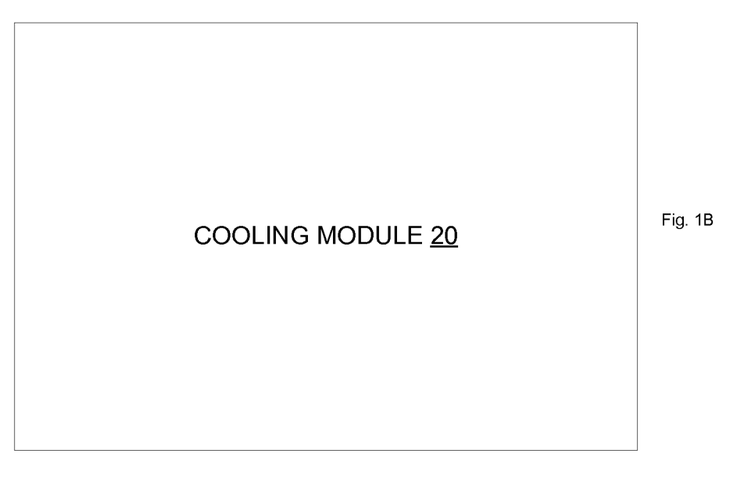

In a second module 20, a cooling system is provided for eradicating Tephritids from fruit. Fruit is isolated and kept isolated during a cooling system process, either with screening fine enough to exclude Tephritids from re-infesting the fruit or in a sealed refrigerator type ocean going container or in a sealed refrigerated type building. If the cooling is done in a refrigerated shipping container then the doors would simply be sealed. If the cooling is done in a refrigerated type building then screening between the building's doorway and a sealable refrigerator type shipping container is placed in such a way to insure that no Tephritids could re-infest the fruit.

Figure 2:
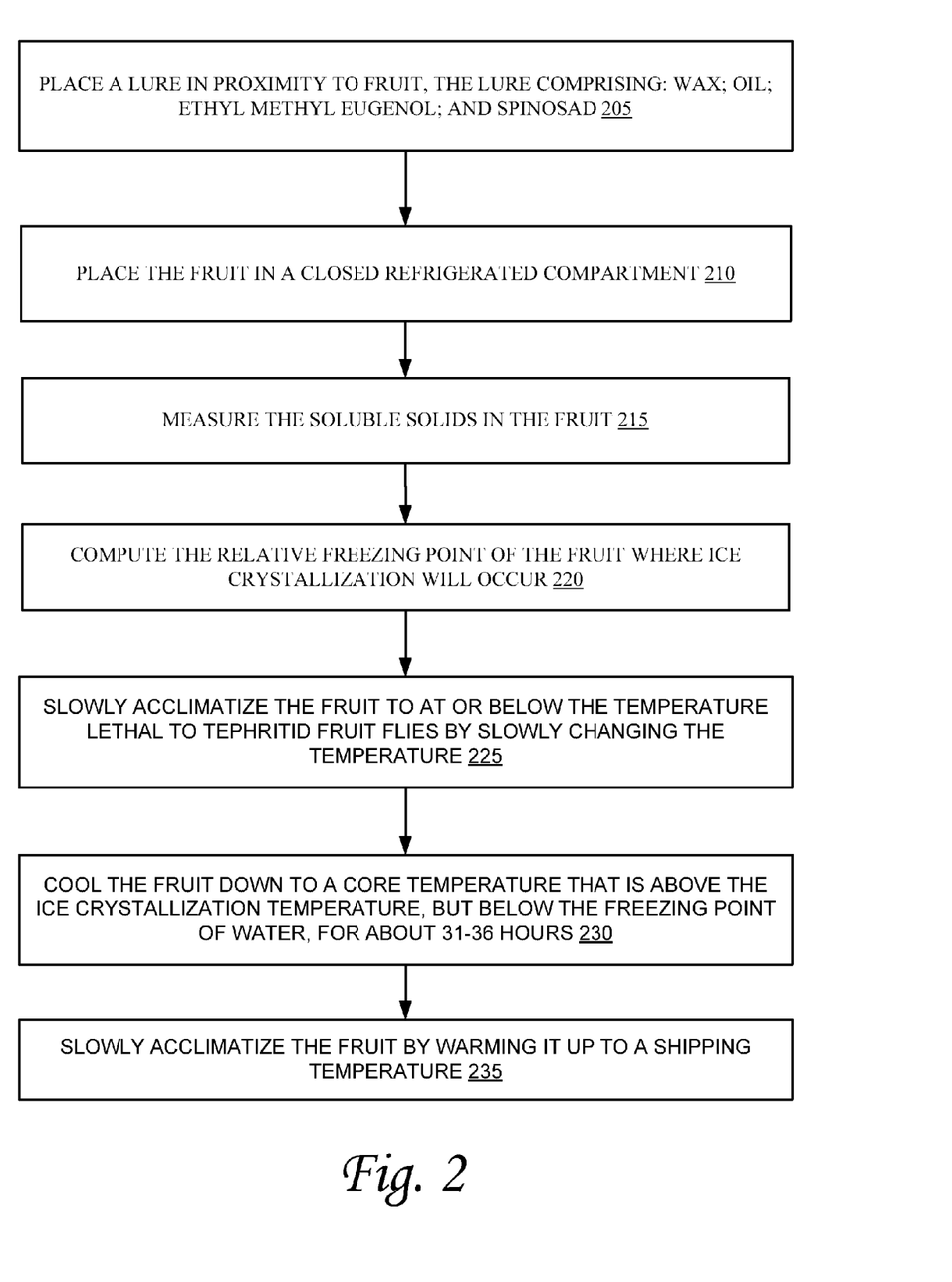
FIG. 2 is a flow chart of a method of controlling tephritid fruit flies.

In a variant, referring to FIG. 2, the process comprises the following steps: Placing 205 a lure comprising: wax; oil; ethyl methyl eugenol; and Spinosad in proximity to fruit growing in a farm, orchard, vineyard or ranch area, and placing 210 the fruit in a closed refrigerated compartment, without necessarily a lure.

In a step 215, measuring the soluble solids in the fruit. In addition, the total dissolved solids may be measured. Then, in a step 220, the relative freezing point of the fruit where ice crystallization will occur is computed.

In a step 225, slowly acclimatize the fruit to chill by slowly changing the temperature.

In a step 230, cooling the fruit down to a core temperature that is above the ice crystallization temperature, but below the freezing point of water, for about 31-36 hours or optionally the time period required for a-yet-to-be-USDA-APHIS approved sub-freezing quarantine protocol.

In a step 235, slowly acclimatize the fruit by warming it up to shipping temperature, which may be 34-40 degrees Fahrenheit, similarly as in the cooling process.

Figure 3:
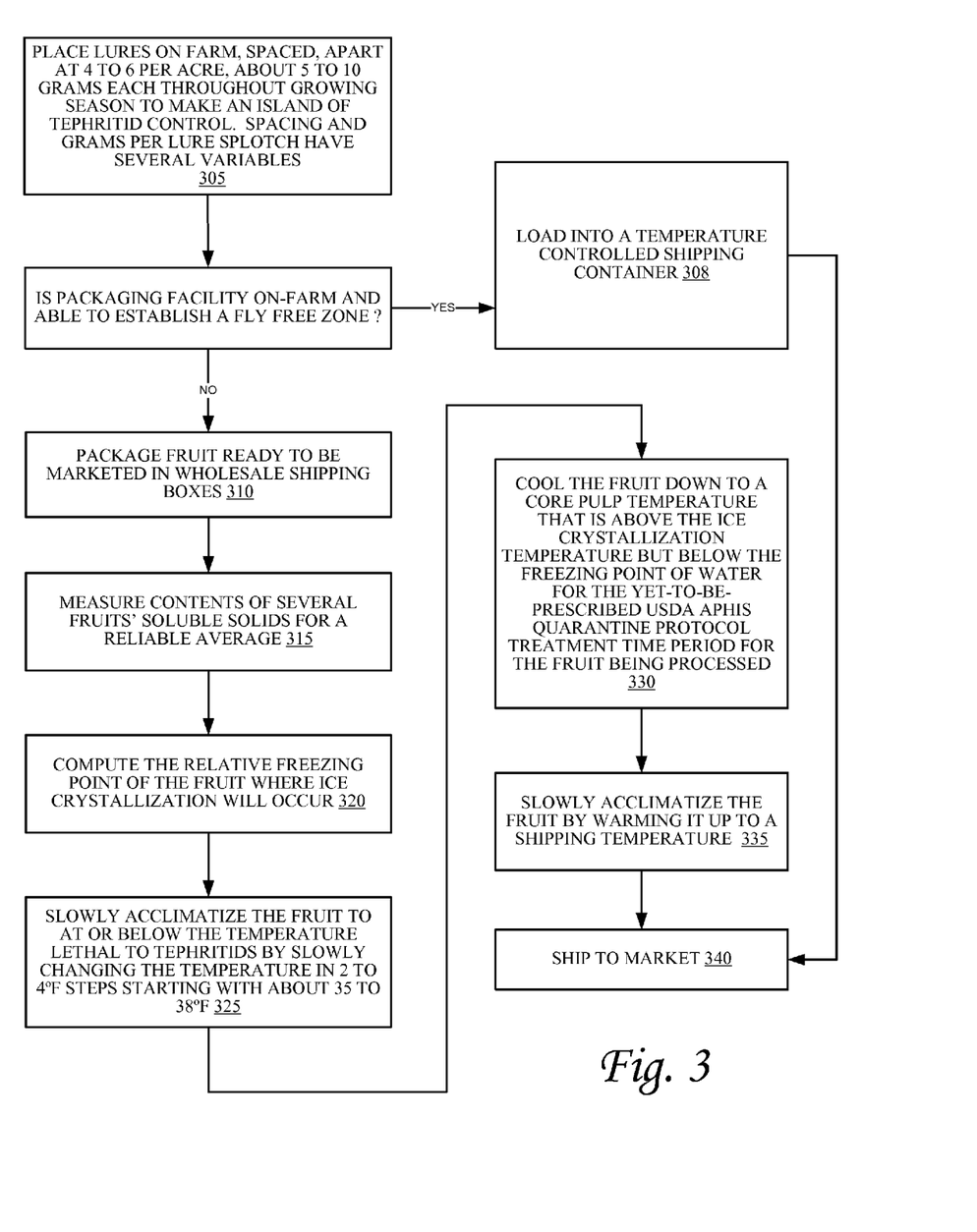
FIG. 3 is a flow chart of a process of eradicating fruit flies.

In a another variant, referring to FIG. 3, the process of eradicating fruit flies comprises the following steps: Placing 305 lures on farm ranch, vineyard, orchard, or similar area, well spaced, and at 4 to 6 per acre, and about 5 to 10 grams each throughout the growing season to make an island of Tephritid control. Spacing and grams per lure splotch have several variables. If the fruit packaging facility is on-farm and are able to establish a fly free zone similar to Florida's Caribbean fly free zone then one may not need the subfreezing protocol, proceed to step 308, otherwise proceed below to step 310. In a step, load 308 into a temperature controlled shipping container such as a sealed refrigerated ocean or truck type container that precludes Tephritid reinfestation. Then ship to market 340.

Figure 14:
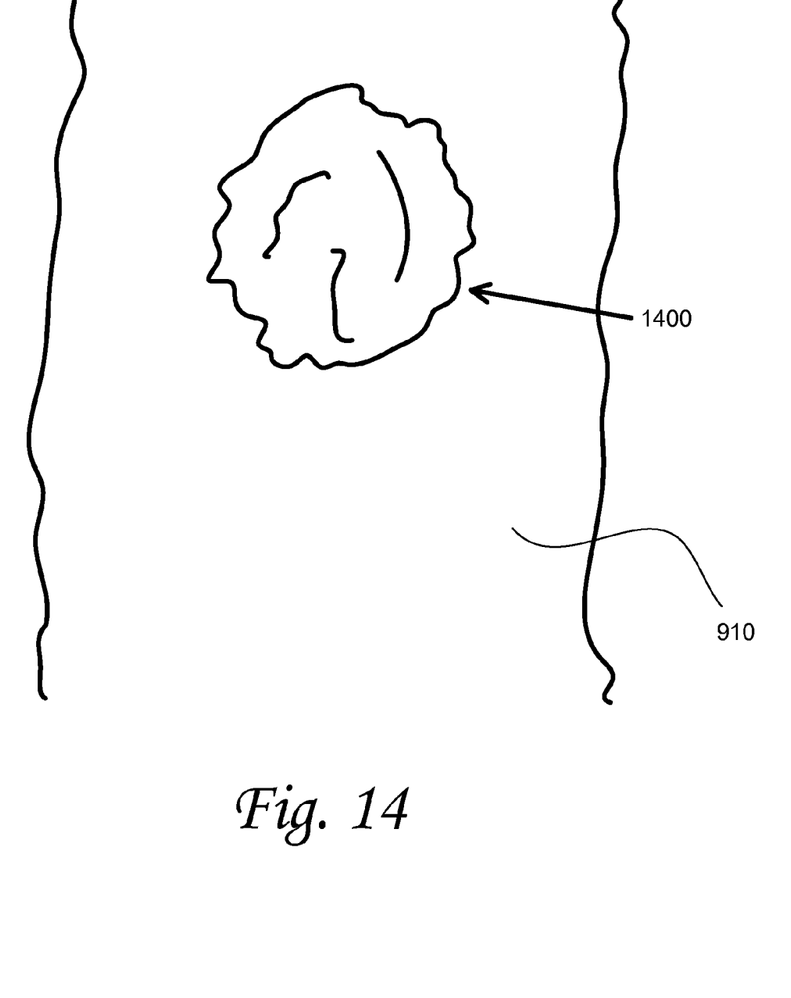
FIG. 14 an example application of lure on an object.

Package 310 fruit ready to be marketed in wholesale shipping boxes see e.g. FIG. 14. Measure 315 several fruit's soluble solid's contents for a reliable average. Compute 320 the relative freezing point of the fruit where ice crystallization will occur. Slowly acclimatize 325 the fruit to at or below the temperature lethal to Tephritids by slowly changing the temperature in 2 to 4° F. steps starting with about 35 to 38° F. Cool 330 the fruit down to a core pulp temperature that is above the ice crystallization temperature but below the freezing point of water for the yet-to-be-prescribed USDA APHIS quarantine protocol treatment time period for the fruit being processed. Slowly acclimatize 335 the fruit by warming it up to a shipping temperature. Ship 340 to market.

For high brix produce in 24 to 48 hours, or optionally the time period required for a-yet-to-be-USDA-APHIS approved sub-freezing quarantine protocol, after attaining 26 to 31.5 degrees core temperature to be able to ship produce to otherwise prohibited quarantined markets. Currently approved cooling systems require 14 or 15 days at 34 degrees, which means there will be considerable fruit breakdown (also known as rotting) at destination. The present cooling treatment system will not work for low brix agricultural crops such as lettuce or zucchini.

In another variant, the system cools the ambient air to between 26 degrees F. and 32 degrees F.

In another variant, the Fruit Fly lure the comprises the following components for a *Bactrocera* (previously known as genus "*Dacus*") *dorsalis* (Oriental fruit fly) lure:

1. Bee's wax, by weight 36.4%
2. Mineral oil, by weight 44.4%
3. Ethyl methyl eugenol also known as methyl eugenol or lure, by weight 10.3%
4. 1-OCTEN-3-OL 0.12%
5. Spinosad, by weight 7.7%
6. Unscented liquid dishwashing soap such as Palmolive—just a few drops These proportions can be varied about the number presented here.

In a variant, a lure for attracting tephritid fruit flies comprises: a wax; a wax thinning agent; a chemical tephritid lure; and a toxicant for tephritids. Optionally, the wax thinning agent is methyl eugenol. In another variant, the wax thinning agent is basil oil. In further variant, the lure comprises: a ratio of wax to wax thinning agent by weight of about 0.8188 to 1.0; a ratio of toxicant to wax thinning agent by weight of 0.0966 to 1.0; and 1 milliliter of toxicant per 5.65 grams of wax.

A method of manufacturing lure, comprises: In a double boiler barely melt the wax. In a separate jar mix the lure's attractant with spinosad adding a few drops of dishwashing soap, watching the miscibility. As the wax melts add the mineral oil with an electric whisk/beater type tool and mix very well beating in as much air as possible. As the mixture cools notice a semi-hardening.

As the wax/oil mixture is in the soft but hardening stage add the lure/spinosad/soap whipping all ingredients together beating in as much air as possible. Keep beating until the mixture is too hard the whisk to beat by hand. Ensure that the whisk is moved all around to make the lure is as homogenous as possible. Let the mixture sit until it settles which takes 12 to 24 hours.

There exists other lures, pheromones, or lure combinations for other Tephritids. Methyl eugenol also attracts *Dacus zonatus* which is another serious Tephritid to be controlled by our lure system. Trimedlure attracts the Mediterranean fruit fly with capilure acting something like an extender for Trimedlure. Ceratitislure is generally for *Ceratitis cosyra*, Questlure is for *Ceratitus rosa* as well as *C. captita* and *C. cosyra*. The ability of this base to control the volatilization of these various insect lures and toxicants is the over riding benefit of this invention which can be combined with a variety of lures/pheromones for targeted pest control.

1-OCTEN-3-OL may attract mosquitoes which can also be incorporated into the base.

The lure/cooling system with various pheromones should control and allow new agricultural markets for areas with the following Tephritid:

*Ceratitis* fruit flies
(*Ceratitis capitata*) ("medfly")
*Ceratitis rosa*
*Anastrepha* fruit flies
*Anastrepha fraterculus*
*A. suspensa* in Florida
Mexican fruit fly (*A. ludens*)
Caribbean fruit fly (*A. suspensa*)
Mexican fruit fly and the West Indian fruit fly (*A. oblique*)
South American fruit fly (*A. fraterculus*)
*Bactrocera* fruit flies
melon fruit fly (*B. cucurbitae*)
Queensland fruit fly, *B. tryoni*
Oriental fruit fly (*B. dorsalis*)
guava fruit fly (*B. correcta*)
Philippines (*B. philippinensis*)
olive fruit fly (*B. oleae*) *Bactrocera oleae* (Gmelin)

Other species that presently assigned to the *Dacus* genus that in the future may be reassigned to the genus *Bactrocera* or other genera, may also be controlled by the system of the present invention.

A novelty of the lure system of the present invention is to control volatilization of lure/toxicant, rain or shine, and that the pests see it as a food, eating it along with the toxicant and exposing new lure/toxicant while eating, killing that pest and preparing a location for the attraction of the next pest. Below is a partial list of insects that can be controlled with this system in table 2.

TABLE 2

| Pest | Common Name | lure | Male | Female | Both Sexes |
|---|---|---|---|---|---|
| A. suspensa | Caribbean fruit fly | Protein | | | X |
| A. ludens | Mexican fruit fly | Protein | | | X |
| A. obliqua | West Indian fruit fly | 9 component blend or protein | | | X |
| A. striata | Guava fruit fly | Protein | | | X |
| A. fraterculus | South American fruit fly | Protein | | | X |
| A. serpentina | Sapote fruit fly | 2 component lure or protein | | | X |
| A. distincta | South American fruit fly | 2 component lure or protein | | | X |
| B. cacuminata | Wild tobacco fly, Solanum fruit fly | Methyl Eugenol AKA EME | X | | |
| B. cucumis | Cucumber fly | ? Possibly protein baits | ? | ? | ? |
| B. cucurbitae | Melon fly | Cuelure | X | | |
| B. dorsalis | Oriental fruit fly | Methyl Eugenol AKA EME | X | | |
| B. frauenfeldi | Mango fruit fly | Cuelure | X | | |
| B. invadens | Asian fruit fly, Mouche des fruits | Methyl Eugenol AKA EME | X | | |
| B. jarvisi | Jarvis' fruit fly | ? Cuelure, protein baits | X | ? | ? |
| B. latifrons | Malaysian fruit fly | ? Maybe protein baits | ? | ? | ? |
| B. musae | Banana fly | Methyl Eugenol AKA EME | ? | | |
| B. neohumeralis | Lesser Queensland fruit fly | Cuelure | X | | |
| B. newmanii | Newman fly | Cuelure | X | | |
| B. oleae | Olive fruit fly | ? | ? | ? | ? |
| B. opiliae | No common name - sibling species to Oriental fruit fly | Methyl Eugenol AKA EME | X | | |
| B. papayae | Papaya fruit fly | Methyl Eugenol AKA EME | X | | |
| B. tyroni | Queensland fruit fly | Cuelure | X | | |
| B. zonata | Peach fruit fly, Guava fruit fly | Methyl Eugenol AKA EME | X | | |
| C. capitata | Mediterranean fruit fly | Capilure | X | | |
| C. capitata | Mediterranean fruit fly | Trimedlure | X | | |
| C. capitata | Mediterranean fruit fly | Questlure | | X | |
| C. cosyra | Marula fruit fly | Ceratitis Lure | X | | |
| C. cosyra | Marula fruit fly | Questlure | X | X | |

TABLE 2-continued

| Pest | Common Name | lure | Male | Female | Both Sexes |
|---|---|---|---|---|---|
| C. rosa | Natal fruit fly | Questlure | | X | |
| | Mosquitoes | 1-Octen-3-ol | ? | ? | ? |
| | Cockroach | Methyl eugenol AKA EME | ? | ? | ? |

Other lure blends include a 9 component blend—ethyl butyrate, isopropyl butyrate, hexan-1-ol, propyl butyrate, isobutyl butyrate, ethyl hexanoate, isopentyl butyrate, ethyl benzoate, and ethyl octanoate; a 2 component lure—ammonium acetate and putrescine; a 3 component type lure containing ammonium acetate, trimethylamine, and putrescine; and a Protein lure. Protein baits may include some kind of yeast like Torulla or hydrolyzed yeast such as brand name Staley's Yeast bait.

The following toxicants were successfully incorporated into lure base and tested: 1. Malathion 2. Spinosad 3. Rotenone 4. Pyrethrin 5. Veratrine 6. Osthole 7. Stemonine 8. *celastrus angulatus* 9. Toosandanin 10. Matrine 11. basil oil.

The following lures were successfully incorporated into lure base and tested: 1. methyl eugenol AKA EME & ME 2. Trimedlure 3. Cuelure 4. Capilure 5. 1-Octen-3-ol.

The following thinning agents were successfully incorporated into wax and tested: 1. mineral oil 2. basil oil 3. methyl eugenol. Some substances may be in more than one class of substance, e.g. toxicant and thinner.

Figure 4:
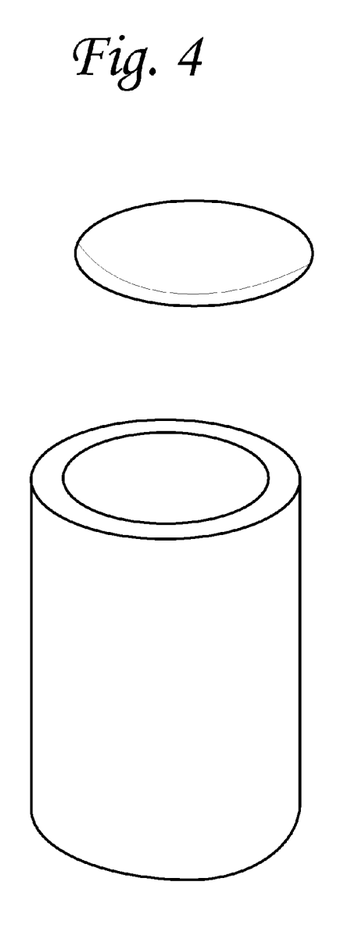
FIGS. 4 and 5 are example containers for lure.
Figure 5:
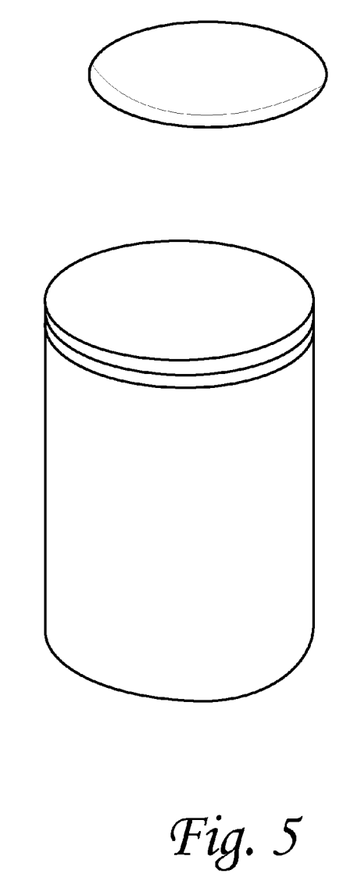

In a variant, referring to FIG. 4, containers for the lures may be tamp-on paint can 405 type 1 pint to 1 gallon sizes having tamp on lids for mating with a rim of a paint can body. Optionally, referring to FIG. 5, a threaded 55 gallon bucket 505 with threaded lid may be provided. Optional variations may have paint stick or tongue depressions may be used to spread a splotch of lure. An air powered grease gun may optionally be used to apply or shoot lure onto desired surfaces, such as, for example, telephone poles. For aerial applications, popcorn sized units, or smaller, of lure may be spread by airplane over large areas.

Figure 6:
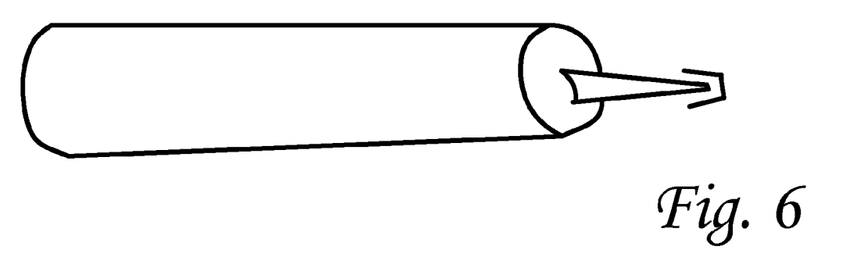
FIGS. 6 and 7 are example dispensing devices for lure.
Figure 7:
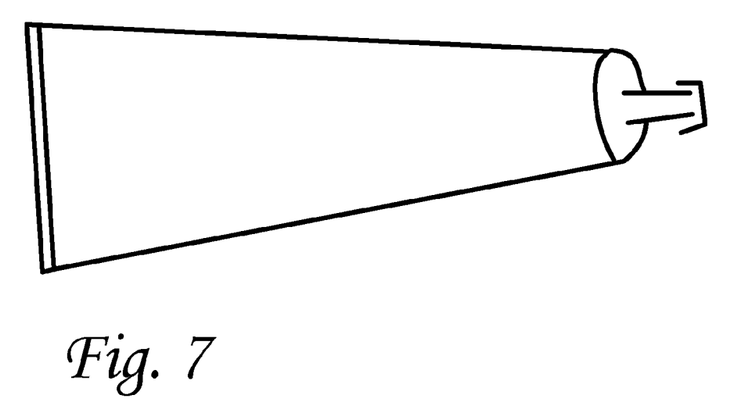

Optionally, referring to FIG. 6, caulking gun 605 type dispensers may be employed to apply lure. Optionally, referring to FIG. 7 toothpaste 705 type dispensers may be employed to apply lure.

Figure 8:
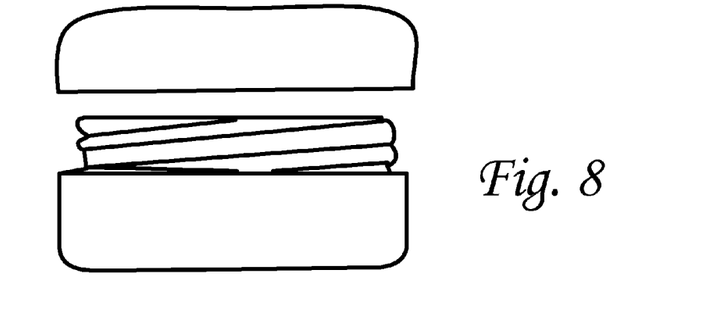
FIG. 8 is an example dispensing jar for lure.

In another variant, referring to FIG. 8, cosmetic type shallow round jars with threaded caps may optionally include double sided sticky tape or glue to affix the jar to a tree, stake in the ground, fence, building or other structure. To operate the lure, the jar is opened exposing lure and the jar is affixed to a surface.

In one example, referring to FIG. 14, lure may be placed on a tree, bush, utility pole, stake in the ground, fence post or similar structure. 5 to 10 grams of lure may be applied to the structure with a paint stick, caulking gun, tooth paste type tube, automatic grease gun to either shoot from a distance from, for example, a moving vehicle to utility poles or up close while on foot.

Figure 9:
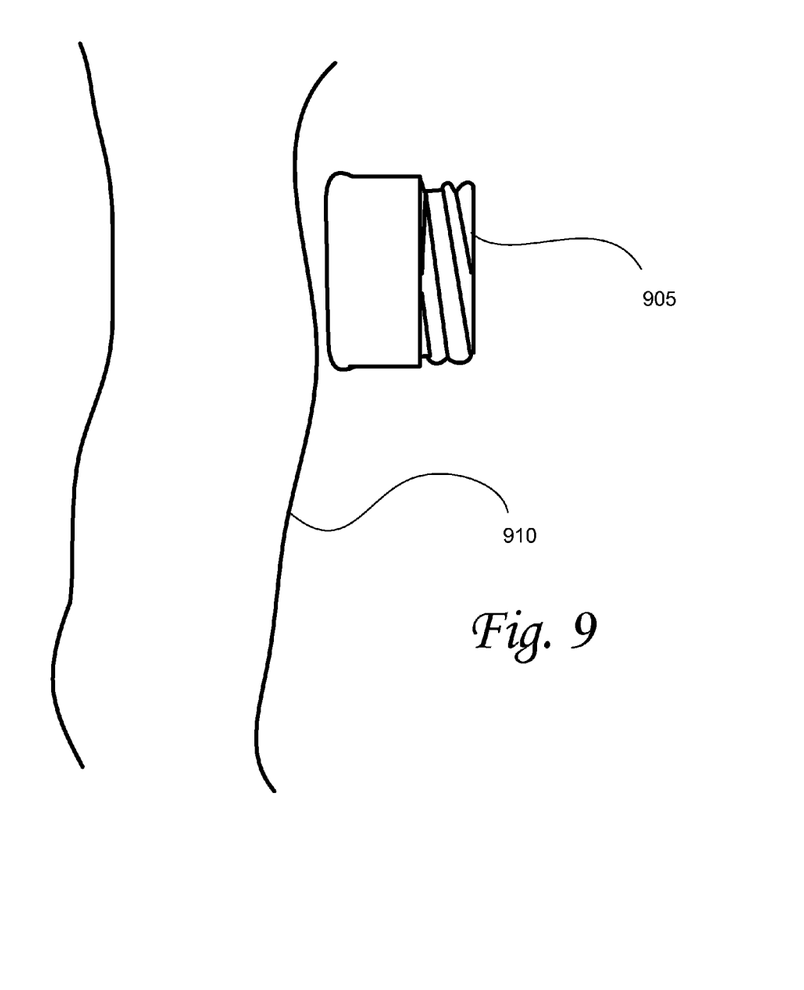
FIG. 9 is an example application of a jar of lure.

Optionally, referring to FIG. 9, the jar 905 may be placed on a tree 910 or other object. When luring fruit flies away from fruit is desired, the jar is opened, exposing the lure.

Figure 10:
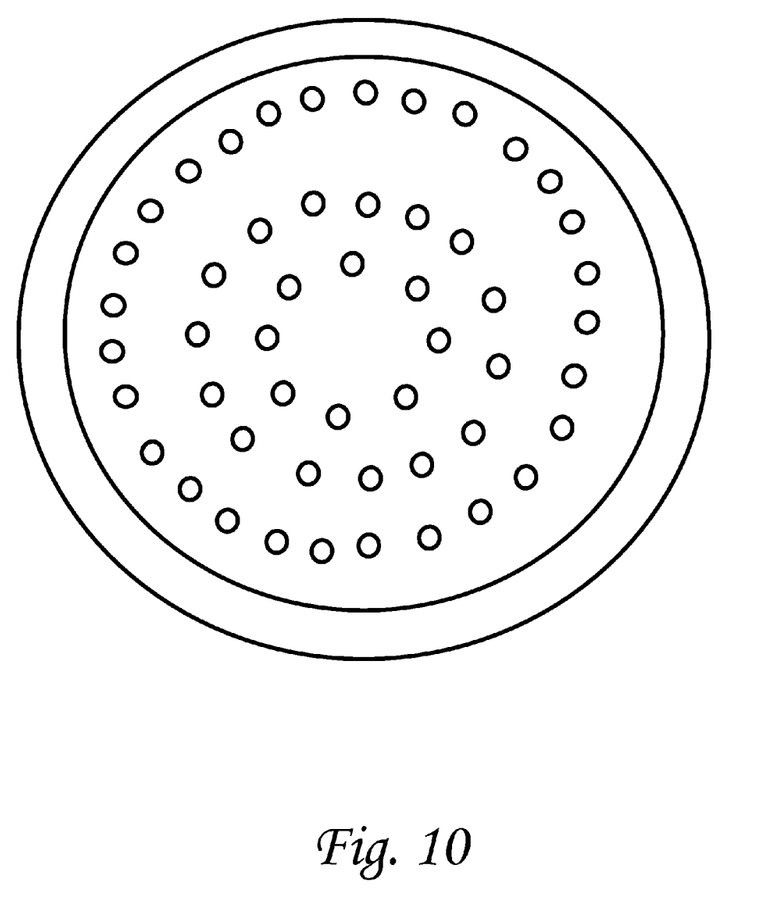
FIGS. 10 and 11 is an example die for casting the lure into usable shapes for dispersal.
Figure 11:
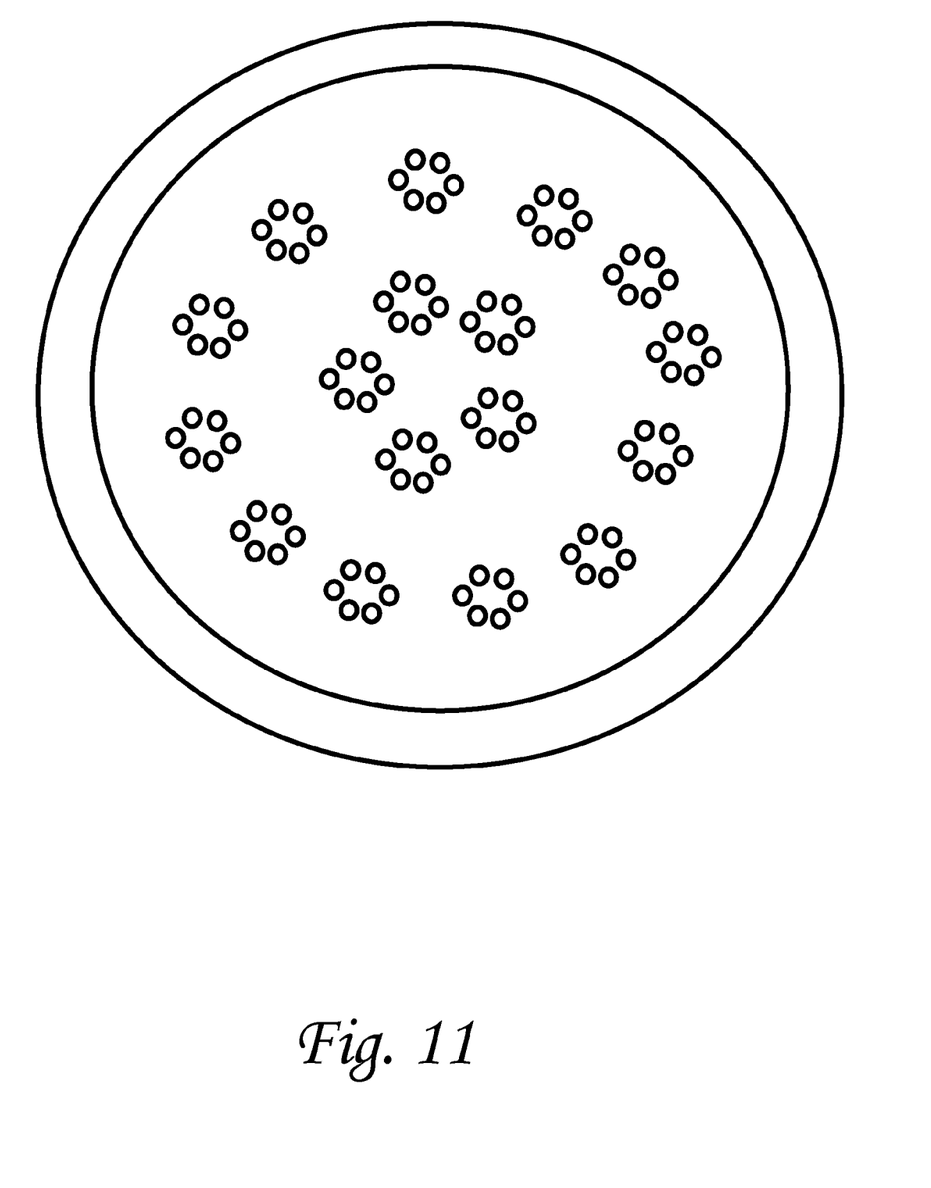

In another variant, referring to FIGS. 10 and 11, dies of various hole sizes for extrusion of lure, may be employed to generate thin pieces of lure for aerial dispersal of lure Thinner extrusions 1005 increase initial volatilization for rapid knockdown. Thicker extrusions 1105 decrease lure/toxic vitalization for long term control.

Figure 12:
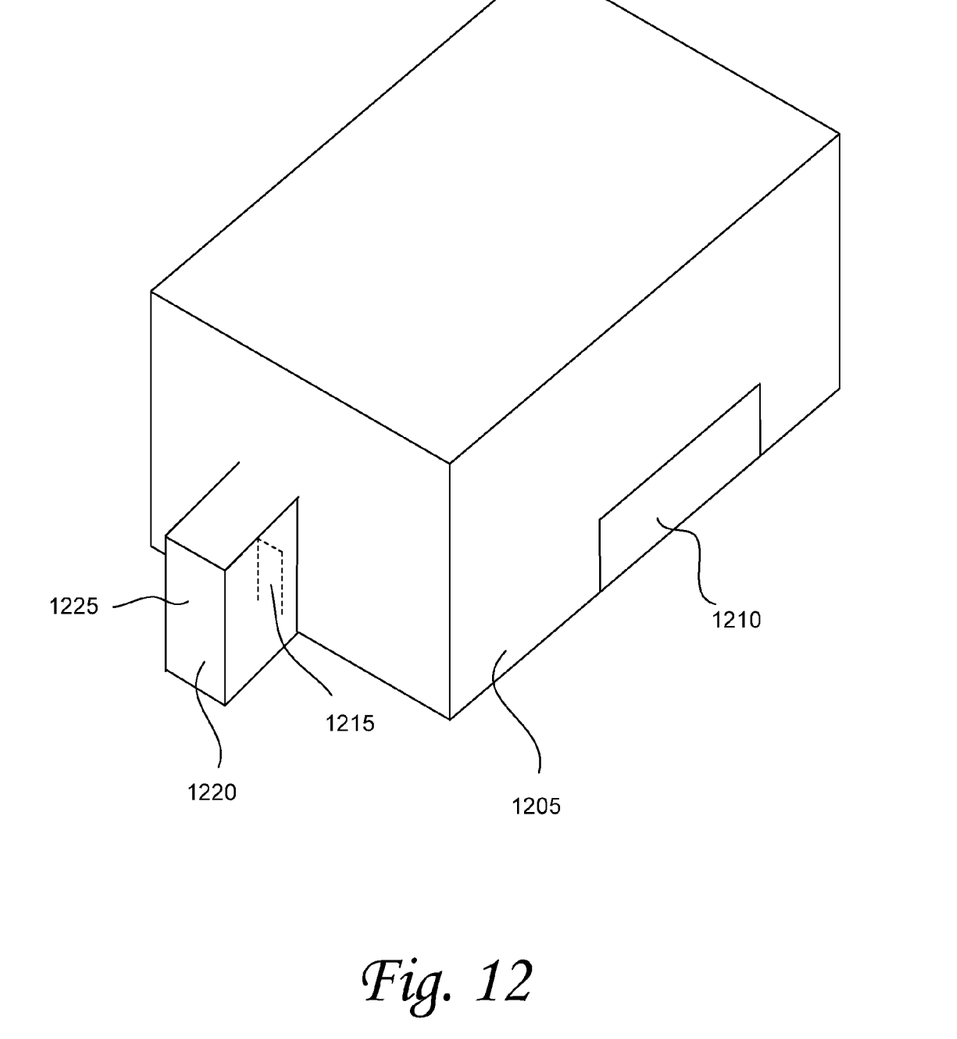
FIG. 12 is an example chill room.
Figure 13:
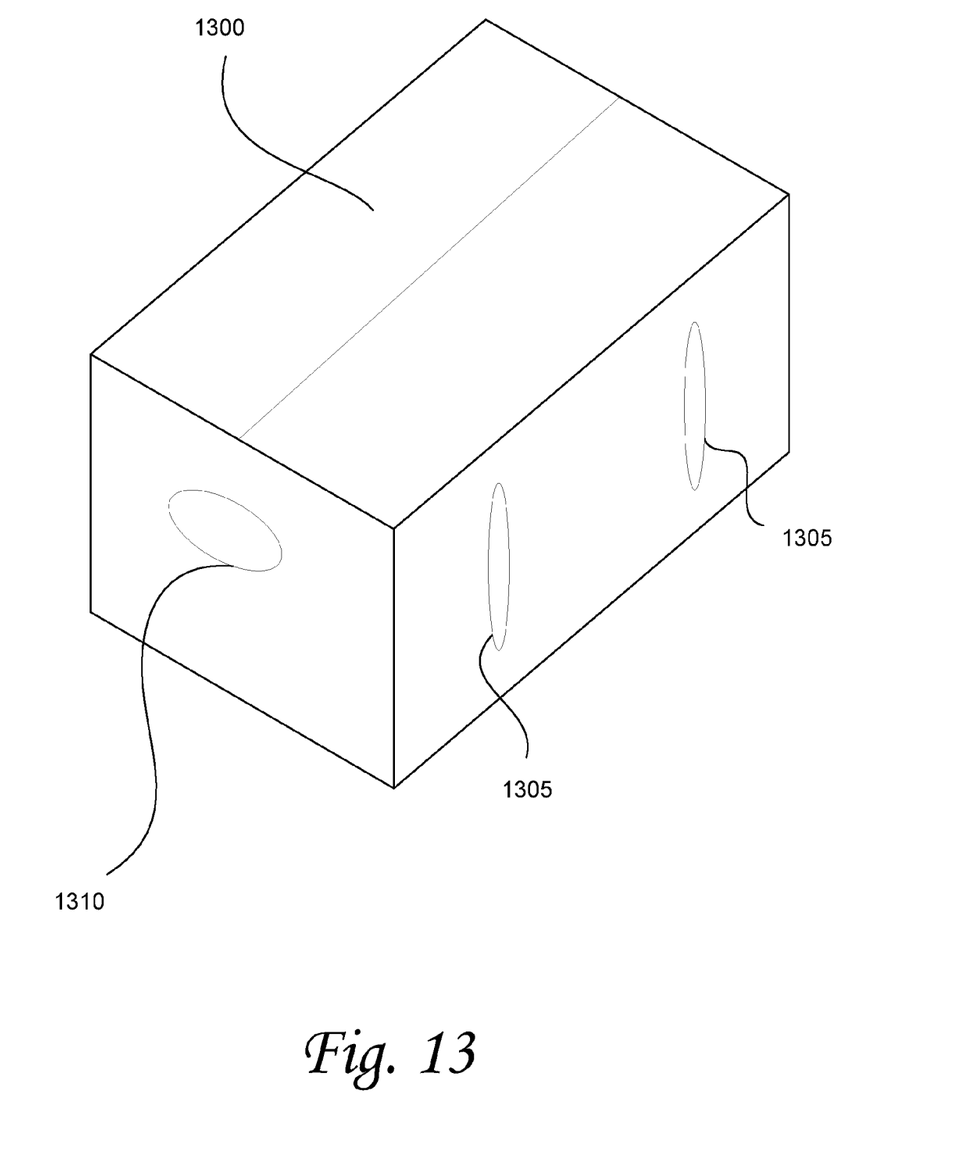
FIG. 13 illustrates an example wholesale shipping box for fruit.

In a further variant, referring to FIG. 13, a chill room 1205 has a truck door 1210 fitted with insect screening to preclude reinfestation of tephritids. The chill room has a double door pedestrian system 1225 having an inner door 1215 and an outer door 1220 to preclude reinfestation of tephritids. Refrigerated containers usually have up to four water drain holes in each corner that either need to be plugged or fitted with a duck bill type rubber one way check valve or equivalent to preclude reinfestation of tephritids.

FIG. 13 illustrates an example wholesale shipping box 1300 for fruit having optional air vents 1305 and an optional handle 1310.

The Tephritid control system of the present invention has the following advantages:

The lure system base controls the volatilization in rain or shine of the both the toxicant and the pheromone.

The target insects actually see the lure as food and eats some of the lure.

When the target insect eats some of the lure then that opens up new bubbles of lure/toxicant to attract the next attracted insect.

For most Tephritids in their mating ritual, the male feeds the female. Thus, if one uses a relatively slow acting poison then the insects feed each other the lure/toxicant, killing many more than otherwise would come to the lure.

The lure system is presently certified for use in organically grown farming systems.

The lure system can utilize cheaper non-organically approved toxicants.

With 5 to 10 gram splotches the system usually lasts about 4 months, or more before all lure is consumed. However, in some cases, lure can be consumed in a much shorter time.

The cooling system uses neither chemicals nor radiation and causes no detectable damage to the fruit but kills Tephritids to open new markets.

Rather than heat up agricultural products to kill Tephritid and then cool the fruit rapidly which does change the crop or product and costs a lot of energy the system of the present invention cools the crop or product down at or a little below freezing. The fruits' soluble solids act as anti-freeze similar to in a car's cooling system to lower the freezing temperature.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A lure for attracting insects, comprising a mixture of: wax; oil; an insect attractant; an insect toxicant; and wherein air is whipped into the mixture to decrease one of or both the toxicant's and the attractant's volatilization.

2. The lure of claim 1 wherein the insect is a tephritid fruit fly.

3. The tephritid fruit fly lure of claim 2, wherein the wax comprises bee's wax and
the oil comprises mineral oil.

4. The tephritid fruit fly lure of claim 2, wherein the lure comprises: a ratio of wax to oil by weight of about 0.8188 to 1.0; a ratio of Spinosad to oil by weight of 0.0966 to 1.0; and 1 milliliter of ethyl methyl eugenol per 5.65 grams of wax.

5. The tephritid fruit fly lure of claim 2, wherein the lure comprises: a ratio of wax to oil by weight from about 0.7711:1.0 to about 0.8694:1.0; a ratio of Spinosad to oil by weight from about 0.0909:1.0 to about 0.1026:1.0 and a ratio of ethyl methyl eugenol to wax of about 1 milliliter of ethyl methyl eugenol per 5.32 grams of wax to about 1 milliliter of ethyl methyl eugenol per 6.00 grams of wax.

6. The tephritid fruit fly lure of claim 2, wherein the lure comprises:
about 36.4% of wax by weight; about 44.4% of oil by weight; about 10.3% of ethyl methyl eugenol by weight; and about 7.7% of Spinosad by weight.

7. The tephritid fruit fly lure of claim 6, wherein the lure comprises about 0.12% of 1-OCTEN-3-OL by weight.

8. A lure configured to reduce tephritid fruit fly populations comprising: wax; oil; ethyl methyl eugenol and Spinosad wherein air is whipped into the mixture to control the toxicant's volatilization.

9. The lure of claim 2, wherein the attractant comprises any one of:
methyl eugenol;
trimedlure;
Ceralure;
capilure;
cuelure;
Spiroacetal;
ammonium acetate and putrescine;
ammonium acetate, trimethylamine, and putrescine;
ethyl butyrate, isopropyl butyrate, hexan-1-ol, propyl butyrate, isobutyl butyrate, ethyl hexanoate, isopentyl butyrate, ethyl benzoate, and ethyl octanoate;
questlure;
Ceratititslure;
a protein bait attractant;
yeast bait attractant;
yeast hydrolysis or yeast hydrolysate;
1-Octen-3-ol;
methanol and ethanol;
methylcyclohexane, nonane, ethylbenzene, and (R)-3-ethyl-4-methylpentanol; and
heptyl butyrate.

10. The lure of claim 2, wherein the attractant comprises a mixture of: methyl acetate, acetic acid, ethyl ester, ethanol, 2-butanone, 3-methyl-acetic acid, 2-methylpropyl ester, 1-propanol, and 2-methyl-3-hydroxy-2-butanone.

11. The lure of claim 2, wherein the attractant comprises a male attractant.

12. The lure of claim 2, wherein the attractant comprises a female attractant.

13. The lure of claim 9, wherein the toxicant comprises any one of:
spinosad; malathion; fipronil; neem oil; pyrethrum; pyrethroid; or naled.

* * * * *